United States Patent [19]

Morris

[11] Patent Number: 4,958,145

[45] Date of Patent: Sep. 18, 1990

[54] BACK INCLINE INDICATOR

[75] Inventor: James A. Morris, Milwaukie, Oreg.

[73] Assignee: Safety Operating Systems, Inc., Lake Oswego, Oreg.

[21] Appl. No.: 348,212

[22] Filed: May 5, 1989

[51] Int. Cl.$^5$ ............................................. G08B 21/00
[52] U.S. Cl. .............................. 340/689; 272/DIG. 5; 340/573; 434/247
[58] Field of Search ................................ 340/573, 689; 272/DIG. 5; 434/247; 273/188 R, 190 A

[56] References Cited

U.S. PATENT DOCUMENTS

| | | |
|---|---|---|
| 3,362,023 | 6/1965 | McMahon . |
| 3,582,935 | 6/1971 | Verhaeghe ............................ 340/573 |
| 3,644,919 | 2/1972 | Mathauser ............................ 340/573 |
| 4,284,986 | 8/1981 | Amortegui ............................ 340/573 |
| 4,536,755 | 8/1985 | Holzgang et al. .................... 340/573 |
| 4,665,388 | 5/1987 | Ivie et al. ............................. 340/573 |
| 4,829,285 | 5/1989 | Brand et al. .......................... 340/573 |

FOREIGN PATENT DOCUMENTS 1547364 6/1979 United Kingdom .
8303747 10/1983 World Int. Prop. O. .

OTHER PUBLICATIONS

Creative Specialists Brochure for Back Box II Lift Angle Sensor.

Primary Examiner—Glen R. Swann, III
Attorney, Agent, or Firm—Olson & Olson

[57] ABSTRACT

A back incline indicator (10) employs a mercury switch (44) and a beeper (72) to indicate to a user (24) whenever the back of the user (24) is bent beyond an acceptable limit, $\lambda$crit. The mercury switch (44) and beeper (72) are attached to a casing (38) including a plate (28A) that is parallel to the back of the user (24). The casing (38) is connected by a connector (14) to the shirt collar of the user (24). The mercury switch (44) is set to an angle $\theta$ from the plate (28A). The value of $\theta$ determines how much the user's back may be bent before $\lambda$crit is reached. The value of $\theta$ may be set to different amounts as the desired value of $\lambda$crit may vary with different uses of the back incline indicator (10).

5 Claims, 2 Drawing Sheets

BACK INCLINE INDICATOR

TECHNICAL FIELD

The present invention relates to position indicators and, in particular, to a position indicator that is worn on a user's back and indicates whenever the user's back is inclined beyond a predetermined level.

BACKGROUND OF THE INVENTION

Millions of dollars are paid by insurance companies each year for back injuries and related workmen's compensation claims. Many of these injuries are caused by persons lifting without bending their knees and sitting with poor posture. Lifting even light packages from a waist high position can cause back injury.

Most back injuries are preventable by proper lifting and correct posture. Many employers have training programs to teach their employees proper lifting and posture techniques. However, following the training employees frequently revert to old habits, and injuries occur. There is a need for a device that indicates whenever the user's back is in an incorrect position so that correct habits may be formed.

SUMMARY OF THE INVENTION

An object of the invention is, therefore, to provide a back incline indicator device that indicates whenever the user's back is in an incorrect position.

Another object of the invention is to provide a back incline indicator device that can be adapted for different users' needs.

A further object of the invention is to provide a back incline indicator that may be worn on a user's shirt collar.

The present invention relates to a back incline indicator that indicates whenever a user's back is bent beyond an acceptable amount. The back incline indicator includes an angle detector that closes an electrical circuit whenever the user's back is bent beyond the acceptable amount. The detector is set at the factory or by the user to a desired angle. The back incline indicator produces an audio signal in response to the circuit being closed.

Additional objects and advantages of the present invention will be apparent from the following detailed description of a preferred embodiment thereof, which proceeds with reference to the accompanying drawings.

DETAILED DESCRIPTION OF PREFERRED EMBODIMENT

Figure 1:
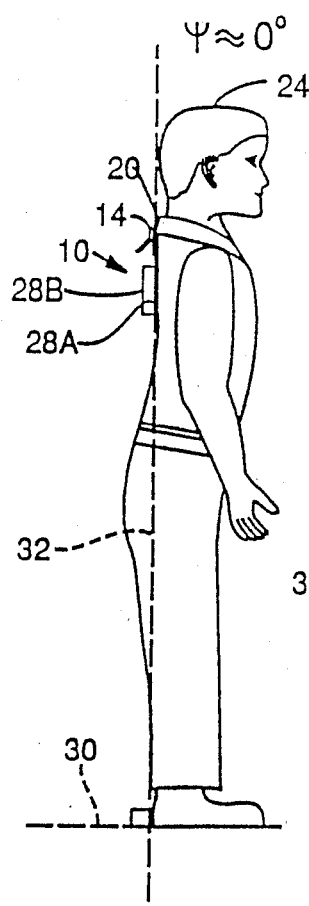
FIG. 1 shows the position of the back incline indicator on a user who is standing straight.

Referring to FIG. 1, back incline indicator 10 is attached by connector 14 to the shirt collar 20 of user 24. Back incline indicator 10 includes plate 28A which rests against the back of user 24 under the force of gravity. Dashed line 30 is parallel to a flat surface (not shown) on which user 24 is standing. Dashed line 32 is at a right angle to dashed line 30. The symbol $\psi$ represents the angle between plate 28A and dashed line 32. Whenever user 24 stands straight, $\psi$ is essentially equal to 0°. The exact value of $\psi$ may vary from user to user.

Figure 2:
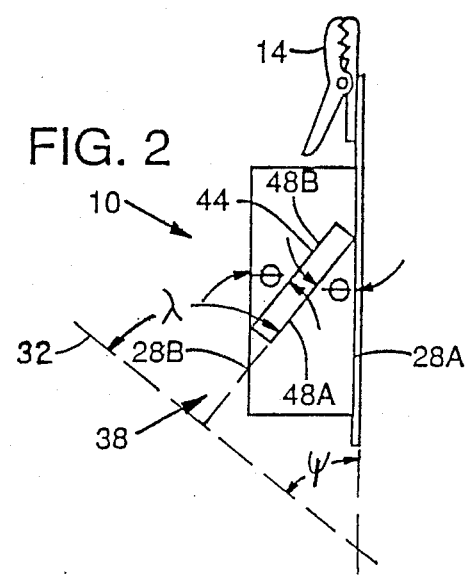
FIG. 2 shows the position of the mercury switch in the back incline indicator.

Referring to FIG. 2, back incline indicator 10 includes casing 38 with side plates 28A and 28B. Casing 38 is preferably made of light weight plastic. The orientation of a mercury switch 44 is shown in casing 38. Mercury switch 44 includes switch sides 48A and 48B. Symbol $\theta$ represents the angle between side 48A and plate 28A, and casing side 48B and plate 28B. The value of $\theta$ is preferably set to a predetermined value. Alternatively, the value of $\theta$ could be variable and set by the user. If $\theta$ is set at the factory, mercury switch 44 could be locked into place by a bracket. If $\theta$ is variable, mercury switch 44 could be held into place by a rotatable screw.

The symbol $\lambda$ represents the angle between switch sides 48A and 48B and dashed line 32. The value of $\lambda$ is described by equation 1 below. It is to be understood that the dashed line 32 in FIG. 2 is a vertical line, as in FIGS. 1, 2 and 4, and that the indicator 10 is tilted as in FIG. 3.

$$\lambda = \theta + \psi \tag{1}$$

Mercury switch 44 allows electrical conduction within a detection circuit whenever $\lambda$, the angle of mercury switch 44, is tilted by more than a critical angle, $\lambda$crit. Otherwise, mercury switch 44 does not allow electrical conduction. Different mercury switches may require different degrees of tilt before the mercury moves.

Connector 14 is preferably a clip, called a bulldog clip and manufactured by Porwake Industries Company, Ltd. Connector 14 is preferably attached to the collar of user 24 for purposes of convenience and the proximity of the collar to the ears so that back incline indicator 10 may be heard. Alternatively, back incline indicator 10 could be strapped to user 24. Back incline indicator 10 is preferably placed on the back of user 24 rather than some other part of the body, e./, the chest. If back incline indicator 10 is positioned on the back of user 24, then whenever user 24 bends forward, back incline indicator 10 will follow the movement of the back of user 24 and the value of $\psi$ will increase. By contrast, if back incline indicator 10 is on the chest of user 24, then $\psi$ will not increase unless both ends of back incline indicator 10 are connected to user 24. Most injuries occur when people are bending forward, so it is important to detect improper forward bending.

Figure 3:
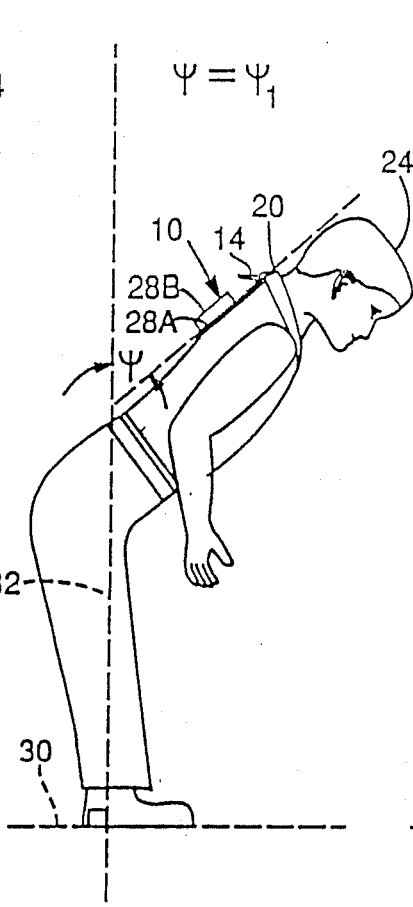
FIG. 3 shows the position of the back incline indicator on a user who is bending improperly.

Referring to FIG. 3, back incline indicator 10 is attached to user 24 while user 24 is reaching down by bending his back without also bending his knees. This is an improper bending technique. The angle $\psi$ is increased to $\psi_1$ as user 24 moves from the position in FIG. 1 to the position in FIG. 3. If $\theta + \psi > \lambda$crit, then mercury switch 44 conducts electricity and back incline indicator 10 signals to user 24 that his bending technique is improper.

Figure 4:
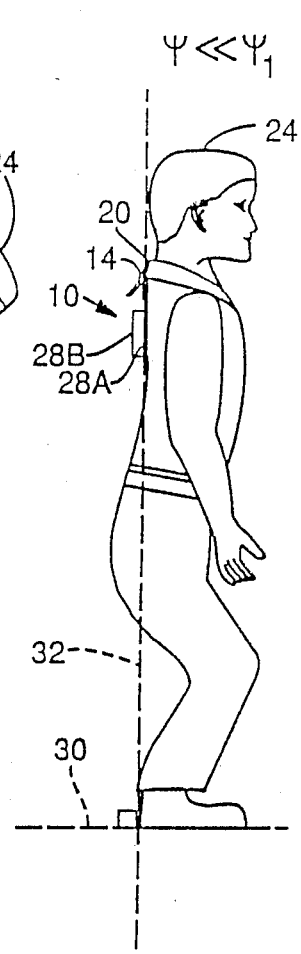
FIG. 4 shows the position of the back incline indicator on a user who is bending properly.

Referring to FIG. 4, back incline indicator 10 is attached to user 24 while user 24 is reaching down by slightly bending his back and substantially bending his knees. The value of $\psi$ is much less than $\theta_1$. Because $\theta + \psi < \lambda$crit, mercury switch 44 does not conduct electricity, and back incline indicator 10 does not signal that an improper technique has been used.

The value of $\theta$ may be set to one value for all purposes, or to different values for particular purposes. Examples of purposes are to learn proper sitting and standing posture, techniques for lifting from the floor, and techniques for lifting from waist height. The value of $\theta$ must not be chosen to be too small or back indicator 10 will inhibit correct back positions.

The value of $\theta$ for learning correct sitting and standing posture would be smaller than for learning to lift from the floor or waist height. The value of $\theta$ for learning to lift from the floor might be greater than for learning to lift from waist height. The value of $\theta$ should be set depending on the particular needs of the user. In addition, the perfect value of $\theta$ may vary from person to person even for a particular purpose. If a single value of $\theta$ is set for all purposes, then compromises will have to be made. A compromise value of $\theta$ equal to 45° is chosen.

Figure 5:
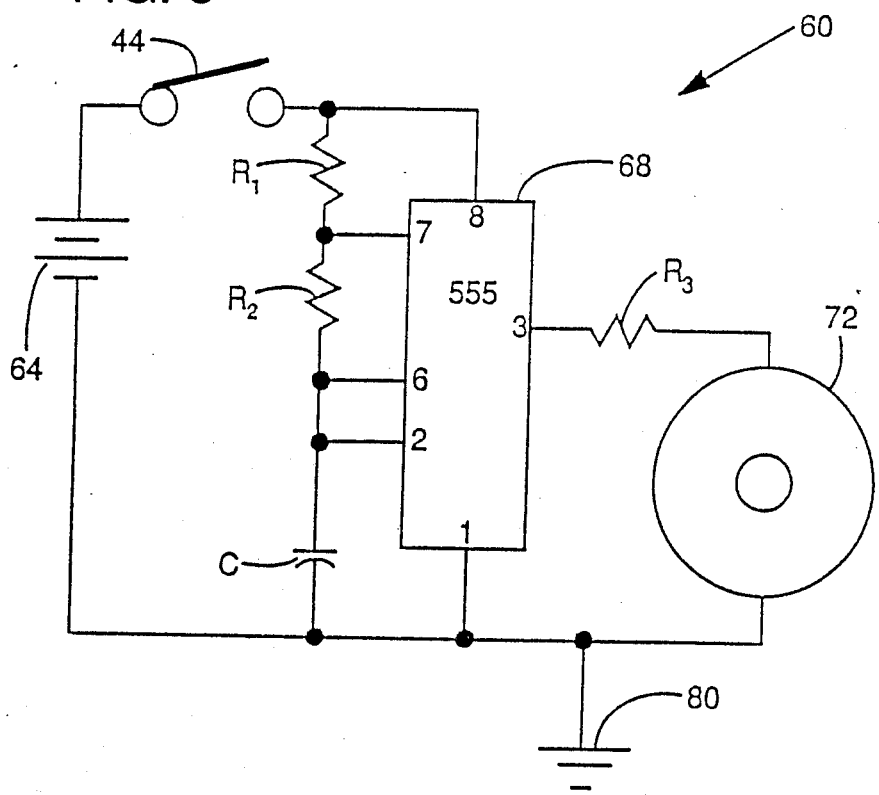
FIG. 5 shows a preferred circuit arrangement for the back incline indicator.

Referring to FIG. 5, electrical schematic 60 of back incline indicator 10 is shown. Whenever mercury switch 44 is tilted greater than the critical angle $\lambda$crit, mercury switch 44 conducts electricity from battery 64 to resistor $R_1$, and pin 8 of timer 68. Timer 68 is preferably a 555 timer that is commonly available through NTE Electronics, Inc. of Bloomfield, N.J.

Timer 68 drives beeper 72 at a volume, duty cycle, pulse rate, and "delay-to-bounce" that are determined by the value of resistors, R1, R2, R3 and capacitor C. An increase in $R_1$ and/or a decrease in R2 results in an increase in the volume and duty cycle of the output of beeper 72. An increase in $(R_1 - R_2)$ and/or in C results in a decrease in the pulse rate. An increase in $R_3$ results in an increase in "delay-to-bounce." Battery 64 is preferably a 7 volt mercury oxide battery, such as Eveready model EP175. Beeper 72 is preferably a 6 volt DC Star HMB-06 audio transducer. Alternatively, beeper 12 could be a 5 volt DC Star TMG-05 audio transducer. With a 6 volt beeper, the pulse rate is $1/[0.7C(R_1+2R_2)]$, and the duty cycle is $0.7C(R_1+R_2)$. C is preferably a 50 volt 0.47 uf capacitor. R1, R2 and R3 are preferably 220K$\Omega$, 47K $\Omega$ and 0-100 $\Omega$, respectively. The pin connections, resistor and capacitor arrangement, and the position of beeper 72 and ground 80 are shown in FIG. 5.

Figure 6:
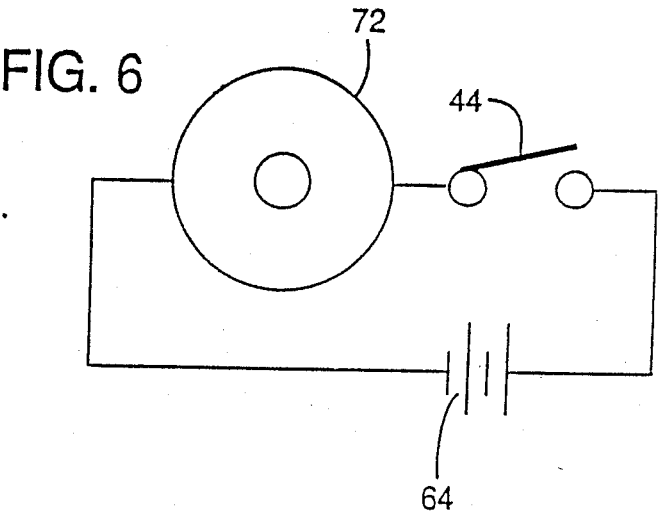
FIG. 6 shows an alternative circuit arrangement for the back incline indicator.

An alternative arrangement for the circuitry in back incline indicator is shown in FIG. 6 in which battery 64, beeper 72 and mercury switch 44 are in series.

It will be obvious to those having skill in the art that many changes may be made in the above described details of the preferred embodiment of the present invention without departing from the underlying principles thereof. The scope of the present invention should be determined, therefore, only by the following claims.

I claim:

1. A back incline indicator for indicating whenever the back of a user is bent beyond an acceptable limit, comprising:
   (a) a hollow casing having a side plate,
   (b) attaching means on the casing for securing the casing to the back of a shirt collar of a user with the side plate resting against the back of the user,
   (c) electric audio signal means in the casing having an electric circuit including a source of electric potential, and
   (d) electric tilt switch means in said electric circuit and mounted in said casing for closing said electric circuit and activating said signal means when said casing side plate is disposed in a plane which forms with a vertical line an included angle of a predetermined magnitude and for opening said circuit and deactivating said signal means when said casing side plate is disposed in a plane which forms with a vertical line an included angle of less than said predetermined magnitude.

2. The back incline indicator of claim 1 wherein the attaching means comprises a clip configured for releasable attachment to a back portion of a shirt collar.

3. The back incline indicator of claim 1 wherein the electric tilt switch means comprises a mercury switch.

4. The back incline indicator of claim 1 including adjustment means interengaging the tilt switch means and casing for adjusting the angular disposition of the tilt switch means relative to the casing side plate, whereby to vary the angle of incline of the back of a user required to activate the signal means.

5. The back incline indicator of claim 1 wherein the electric signal means comprises audio signal producing means, the attaching means is configured for attachment of the casing to the back portion of a shirt collar for effective hearing of the audio signal by the user, and the electric tilt switch means comprises a mercury switch mounted for angular adjustment for varying the angle of incline of the back of a user required to activate the audio signal producing means.

* * * * *

UNITED STATES PATENT AND TRADEMARK OFFICE
CERTIFICATE OF CORRECTION

PATENT NO. : 4,958,145
DATED : September 18, 1990
INVENTOR(S) : JAMES A. MORRIS

It is certified that error appears in the above-identified patent and that said Letters Patent is hereby corrected as shown below:

Col 2, line 46, "$\underline{e}./$" should read --$\underline{e.g.}$--;

Col 2, line 68, "$\theta_1$" should read --$\psi_1$--.

Col 3, line 42, "12" should read --72--.

Signed and Sealed this

Seventh Day of January, 1992

Attest:

HARRY F. MANBECK, JR.

*Attesting Officer*      *Commissioner of Patents and Trademarks*